(12) United States Patent
Weaver et al.

(10) Patent No.: US 12,070,540 B2
(45) Date of Patent: Aug. 27, 2024

(54) WETNESS DETECTOR WITH INTEGRATED INERTIAL MEASUREMENT UNIT CONFIGURED FOR USE IN A DIALYSIS SYSTEM

(71) Applicant: Fresenius Medical Care Holdings, Inc., Waltham, MA (US)

(72) Inventors: Colin Weaver, Pleasanton, CA (US); Martin Crnkovich, Walnut Creek, CA (US); David Yuds, Hudson, NH (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 300 days.

(21) Appl. No.: 17/529,571

(22) Filed: Nov. 18, 2021

(65) Prior Publication Data
US 2023/0149611 A1    May 18, 2023

(51) Int. Cl.
*A61M 1/16* (2006.01)
*A61M 1/36* (2006.01)

(52) U.S. Cl.
CPC ........ *A61M 1/1692* (2013.01); *A61M 1/1601* (2014.02); *A61M 1/3621* (2013.01);
(Continued)

(58) Field of Classification Search
CPC ...... A61B 2562/0219; A61B 2562/029; A61B 5/11; A61M 1/1601; A61M 1/1692;
(Continued)

(56) References Cited

U.S. PATENT DOCUMENTS

| 9,913,608 | B2 | 3/2018 | Lewis et al. |
| 9,928,723 | B2 | 3/2018 | Chen |

(Continued)

FOREIGN PATENT DOCUMENTS

| DE | 112012003387 T5 | 4/2014 |
| EP | 3276515 A2 | 1/2018 |

(Continued)

OTHER PUBLICATIONS

International Search Report and Written Opinion for the Patent Application No. PCT/US2022/047247, mailed Feb. 1, 2023, 18 pages.

(Continued)

*Primary Examiner* — Dirk R Bass
(74) *Attorney, Agent, or Firm* — KDW FIRM PLLC (57) ABSTRACT

A detector assembly configured for use in a dialysis (e.g., a hemodialysis) system is disclosed herein. The detector assembly including a wetness detector configured to detect blood, fluid, a leak, etc. The detector assembly being operatively coupled to, and more preferably, including an inertial measurement unit (IMU). Thus arranged, the detector assembly is configured to measure, read, obtain, provide, etc. additional information or data during a dialysis treatment, which information or data can be transmitted and/or used to, for example, provide greater insight into the system and/or to make better decisions. In one embodiment, the detector assembly can be used to determine when and how a patient is moving and feed that information back to the dialysis machine. In use, the information or data can be used in combination with other information to make an improved determination as to the requirement for an alert and/or stoppage of the dialysis treatment.

12 Claims, 4 Drawing Sheets

(52) U.S. Cl.
CPC . *A61M 2205/18* (2013.01); *A61M 2205/3327* (2013.01); *A61M 2205/3553* (2013.01); *A61M 2205/8206* (2013.01); *A61M 2230/04* (2013.01); *A61M 2230/63* (2013.01)

(58) Field of Classification Search
CPC .............. A61M 1/3621; A61M 1/3656; A61M 2205/18; A61M 2205/3327; A61M 2205/3331; A61M 2205/3553; A61M 2205/3569; A61M 2205/3576; A61M 2205/8206; A61M 2230/04; A61M 2230/06; A61M 2230/63
See application file for complete search history.

(56) References Cited

U.S. PATENT DOCUMENTS

| | | |
|---|---|---|
| 10,388,143 B2 | 8/2019 | Eddy et al. |
| 2018/0206735 A1 | 7/2018 | Holz et al. |
| 2019/0175810 A1 | 6/2019 | Quiroz |
| 2019/0258315 A1 | 8/2019 | Djokovic |

FOREIGN PATENT DOCUMENTS

| | | |
|---|---|---|
| EP | 3304366 A1 | 4/2018 |
| WO | 2020206155 A1 | 10/2020 |

OTHER PUBLICATIONS

2008K@home Wet Alert Wireless Wetness Detector Home User's Guide, 2012-2014, 2016 Fresenius USA, Inc.
International Preliminary Report on Patentability for International Application No. PCT/US2022/047247, dated May 2, 2024, 11 pages.

WETNESS DETECTOR WITH INTEGRATED INERTIAL MEASUREMENT UNIT CONFIGURED FOR USE IN A DIALYSIS SYSTEM

FIELD OF THE DISCLOSURE

The present disclosure generally relates to dialysis machines and systems, and more particularly to a dialysis (e.g., hemodialysis) system including a detector assembly including a wetness detector and an integrated inertial measurement unit.

BACKGROUND

Dialysis machines are known for use in the treatment of renal disease. The two principal dialysis methods are hemodialysis (HD) and peritoneal dialysis (PD). As will be readily appreciated by one of ordinary skill in the art, a hemodialysis system is arranged and configured to, inter alia, pump a patient's blood through a dialyzer. In addition, the hemodialysis system includes a HD machine and one or more containers containing a fluid (e.g., a dialysate), which during use is also pumped through the dialyzer of the HD system simultaneously with the patient's blood. A semi-permeable membrane in the dialyzer separates the blood from the dialysate within the dialyzer and allows diffusion and osmosis exchanges to take place between the dialysate and the blood. Thus arranged, in use, the patient's blood is cleaned or filtered.

Figure 1:
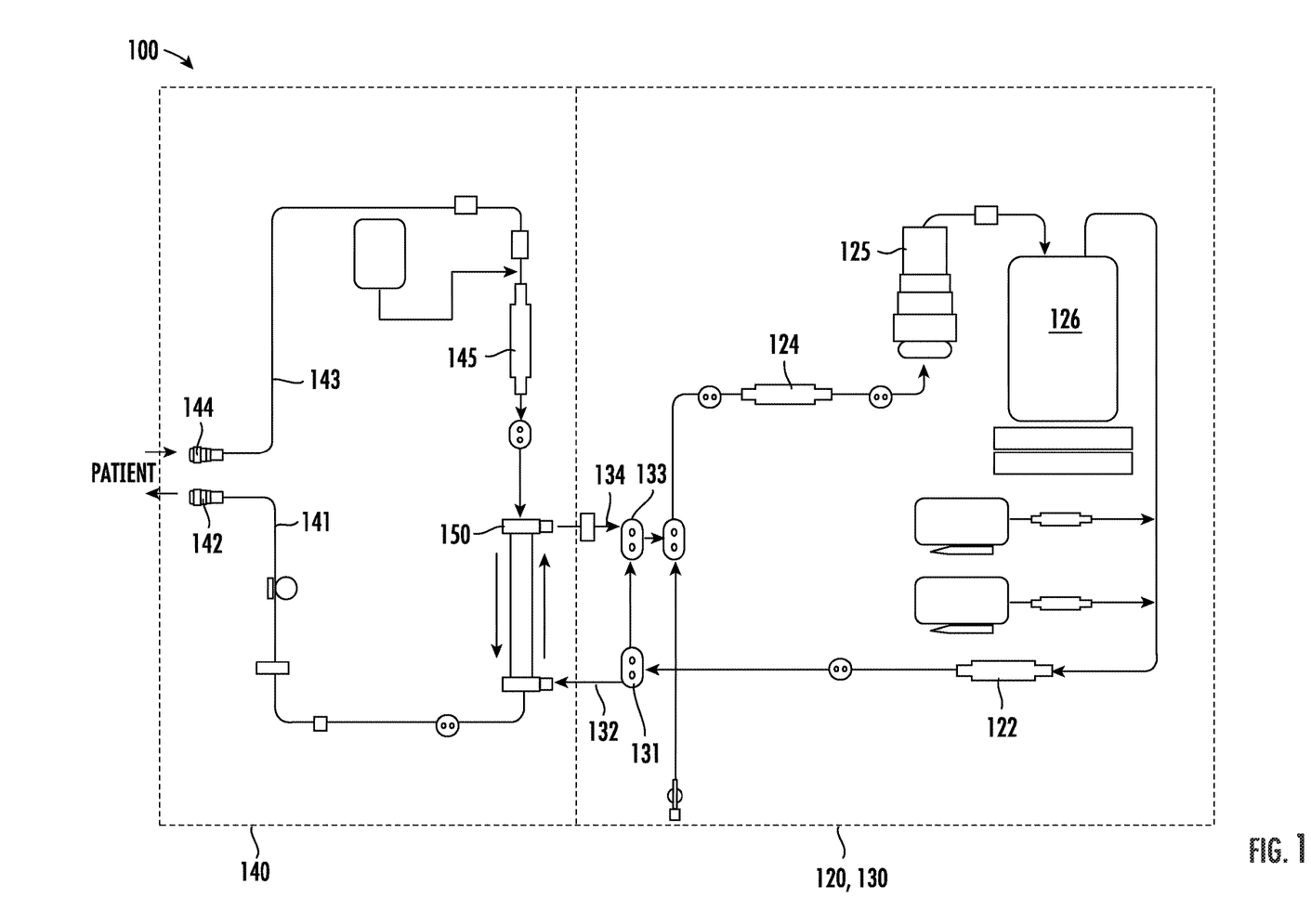
FIG. 1 illustrates an example of an embodiment of a hemodialysis system.

Referring to FIG. 1, as will be readily appreciated by one of ordinary skill in the art, an embodiment of a conventional hemodialysis system 100 is disclosed. As illustrated, the hemodialysis system 100 includes a dialysis machine 120 including a dialysate flow path 130, an extracorporeal blood flow path 140, and a dialyzer 150. In addition, the hemodialysis system 100 may include any number of additional components needed to manage, sense, etc. the flow of dialysate and/or blood through the system 100.

As will be readily appreciated by one of ordinary skill in the art, in use, the dialysis machine 120 and dialysate flow path 130 are arranged and configured to pump dialysate through the dialysate-side of the dialyzer 150. To this end, the dialysis machine 120 may include, inter alia, first and second dialysate pumps 122, 124 to circulate dialysate through the dialysate path 130. In addition, the dialysis machine 120 may include a sorbent cartridge 125 for regenerating used or spent dialysate after it leaves the dialyzer 150. In use, the first and second pumps 122, 124 may move the dialysate through the sorbent cartridge 125 and into a dialysate reservoir 126, out of dialysate reservoir 126, and back through the dialyzer 150. As illustrated, the dialysate path 130 includes an outlet 132 to pump or move the dialysate through an outlet valve 131 and into the dialyzer 150 and an inlet 134 to receive spent dialysate through an inlet valve 133 from the dialyzer 150.

The extracorporeal blood path 140 includes a to-patient connector 142 such as, for example, a needle, at the end of a venous return line 141, a from-patient connector 144 such as, for example, a needle, at an end of an arterial line 143, and a blood pump 145 arranged and configured to pump or pull blood from the patient through the arterial line 143 through the blood side of the dialyzer 150 and back to the patient through the venous return line 142.

In use, the dialyzer 150 includes a cartridge comprising a semi-permeable membrane (e.g., a high flux membrane) arranged and configured to remove toxins from the blood. In one embodiment, the removal of toxins is accomplished by establishing a concentration gradient across the semi-permeable membrane by allowing the dialysate to flow on one side of the membrane in one direction while simultaneously allowing the blood to flow on the other side of the membrane in the opposite direction. The dialyzer 150 may be of any type suitable for hemodialysis, hemodiafiltration, hemofiltration, or hemoconcentration, as are known in the art. Examples of suitable dialyzers include, but are not limited to, Fresenius® F60, F80 available from Fresenius Medical Care of Lexington, Mass., Baxter Conn. 110, CT 190, Syntra® 160 available from Baxter of Deerfield, Ill., or Minntech Hemocor HPH® 1000, Primus® 1350, 2000 available from Minntech of Minneapolis, Minn.

It should be appreciated that while a particular embodiment of a hemodialysis system including a dialysis flow path, an extracorporeal blood flow path, and a dialyzer have been described and illustrated, any number of different hemodialysis systems now known or hereafter developed may be utilized.

Figure 2:
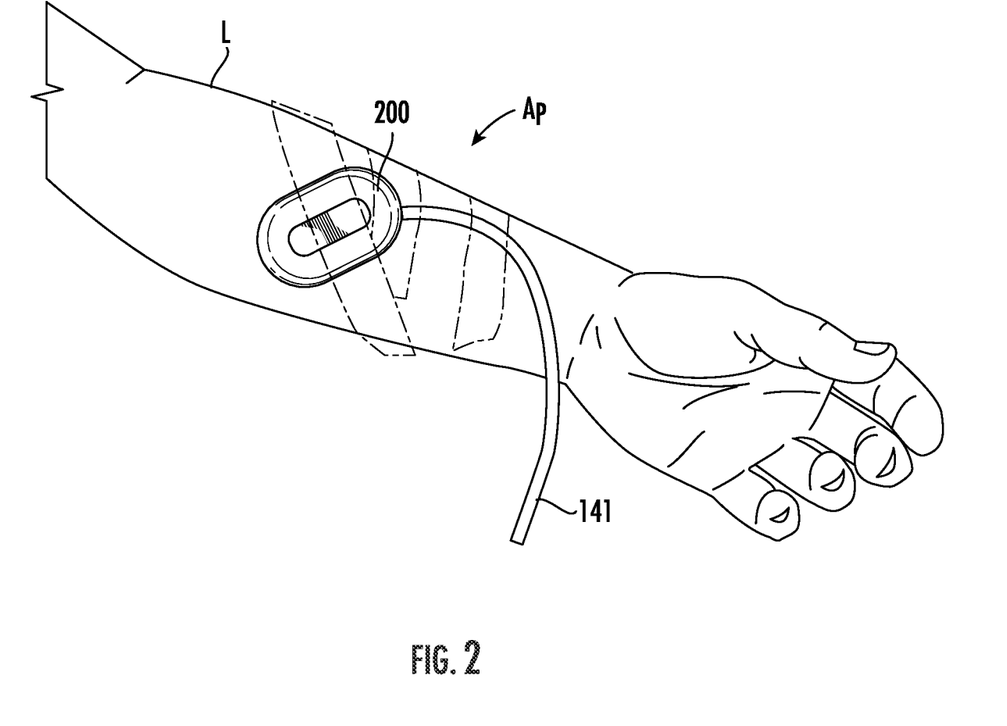
FIG. 2 illustrates an embodiment of a wetness detector (e.g., the WetAlert Wetness Detector) adhered to a patient's blood access point on a patient's limb.

Referring to FIG. 2, a wetness detector 200 for sensing wetness (e.g., blood, a leak, etc.) may be positioned adjacent to the patient's blood access point AP (e.g., adjacent to the to-patient connector 142 (e.g., needle) at the end of a venous return line 141) on a patient's limb L (e.g., arm). As illustrated, in one embodiment, the patient's blood access point AP may be provided on the patient's arm, although this is not necessary.

Figure 3A:
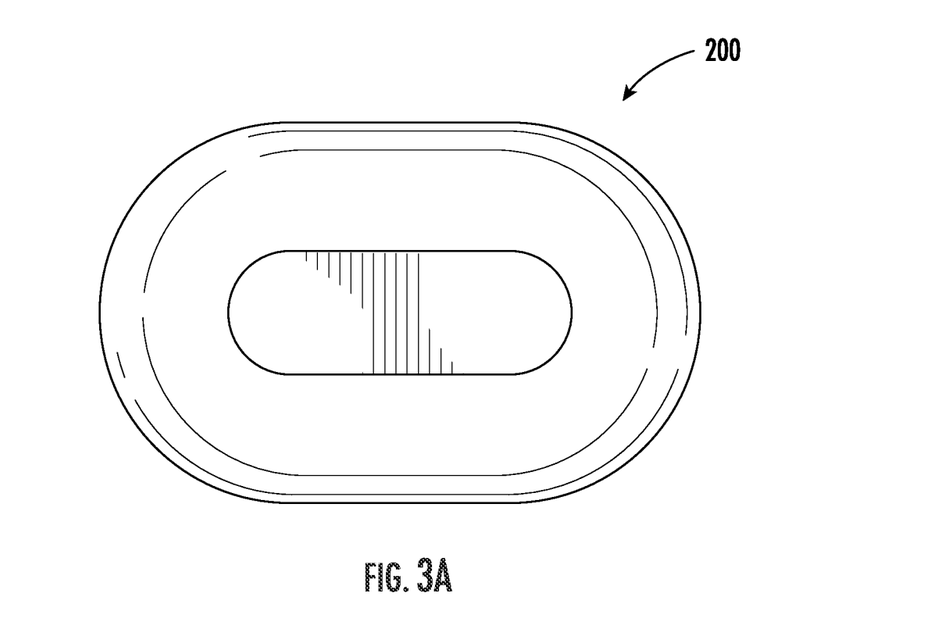
FIGS. 3A and 3B illustrate a top view and a bottom view, respectively, of the wetness detector used in FIG. 2.
Figure 3B:
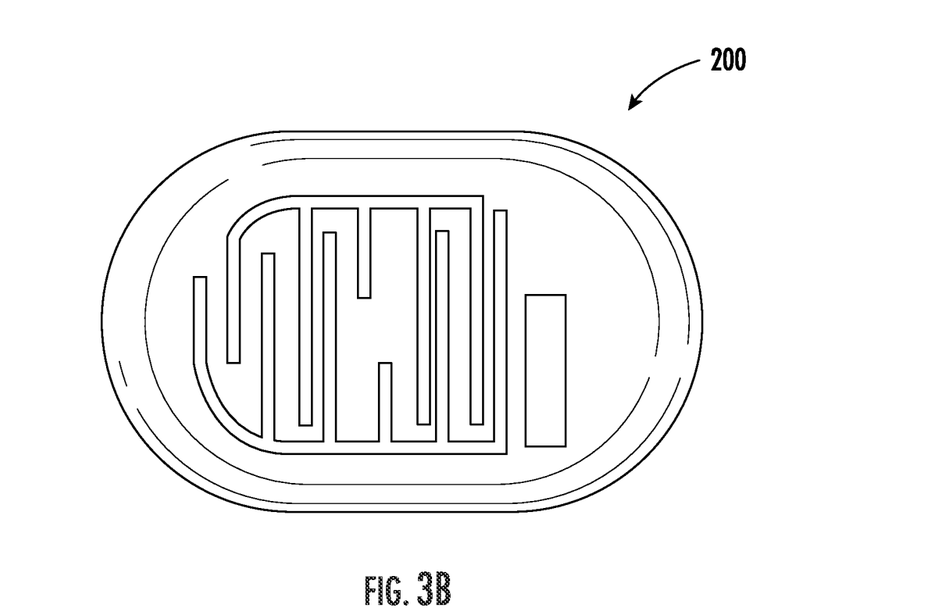

Referring to FIGS. 3A and 3B, in one embodiment, the wetness detector 200 may be the WetAlert Wetness Detector supplied by Fresenius Medical Care. In use, in one embodiment, the WetAlert Wetness Detector is a battery powered sensor that may be adhered (e.g., taped) over the patient's blood access point AP. The WetAlert Wetness Detector is arranged and configured to detect wetness such as, for example, a leak, blood, etc. (e.g., the WetAlert Wetness Detector is a wireless sensor used to detect leaks, wetness, blood, etc. by for example, detecting wetness when the blood bridges two leads on the patient contacting surface of the sensor (as illustrated in FIG. 3B) thereby completing a circuit on the sensor, which causes the sensor to send a signal to the dialysis machine). However, it should be appreciated that this is but one configuration, and alternate sensors or detectors arranged and configured to detect a leak may be used such as, for example, in one embodiment, the sensor may be arranged and configured to detect the color red.

In any event, during a hemodialysis procedure, blood loss from the venous return line 141 may occur if the needle becomes dislodged from the patient's blood access point AP. Needle dislodgement may occur, for example, when a needle slips out of the patient's blood access point AP due to pulling forces on the venous return line 141 or movement of the patient's access limb L. If detection of a leak is determined, the detector such as, for example, the WetAlert Wetness Detector, is arranged and configured to transmit a signal to the dialysis machine, which in response thereto, is arranged and configured to transmit an alarm, stop the blood pump, and/or close the venous bloodline clamp (e.g., valve).

In addition, the dialysis system may monitor a patient's pulse. For example, the dialysis system may include a cuff or a pulse oximeter attached to a patient's limb for measuring a patient's pulse. In one embodiment, the dialysis system may continually monitor the pressure of the arterial and venous bloodlines for either abrupt changes in pressure or a slow departure from soft and hard pressure limits that could indicate clotting, kinks in the tubing, or a potential needle dislodgement.

In use, if a change in a patient's pulse is detected (e.g., in the event a patient's pressure falls below or rises above predetermined or settable alarm limits), the dialysis machine and/or system may interpret changes in the pressure of the patient's pulse that fall outside of an allowable range as a potential needle dislodgement causing an alert to be transmitted and/or stoppage of the dialysis treatment (e.g., the dialysis system sounds an alarm, stops the blood pump, and closes the venous blood line clamp).

One disadvantage of the current hemodialysis system including the WetAlert Wetness Detector is that patient's movements can affect pressure readings, which may lead to false nuisance alarms. For example, if a patient moves too quickly, the dialysis machine and/or system may interpret the change in pressure caused by the patient's movements as a potential needle dislodgement and sound the alarm and/or stop the blood flow, which may adversely affect the patient's treatment and/or sleep. For example, if a patient's raises an access limb L too high in the course of normal activities or drops an access limb L too low in the course of normal activities, the dialysis machine and/or system interprets the change in pressure caused by the patient's movements as a potential needle dislodgement and sounds the alarm and/or stops the blood flow. However, the change in pressure may be caused by a patient's movement occurring while the patient is sleeping and not because of a needle dislodgement. In addition, if the patient is the operator of the dialysis machine during, for example, an at home treatment, the patient now needs to reach over and clear the alarm on the dialysis machine, which action may itself lead to needle dislodgements.

It would be beneficial to provide a system that knows (e.g., can determine) what the patient's access limb L was doing prior to and during signal anomalies caused by changes in pressure of the patient's pulse to minimize the likelihood of false nuisance alarms. Additionally, it would be beneficial for the detector and/or system to provide secondary information or data. For example, it would be beneficial to know how long the detector has been sitting on a shelf or how often or long the detector has been used. It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a dialysis system for providing a dialysis treatment to a patient is disclosed. In one embodiment, the dialysis system comprises a dialysis machine including a dialysate flow path; an extracorporeal blood flow path including a connector coupled to a limb of the patient at a blood access point; a dialyzer arranged and configured to receive dialysate from the dialysate flow path and blood from the extracorporeal blood flow path; and a detector assembly coupled to the limb of the patient adjacent to the blood access point. In one embodiment, the detector assembly includes a wetness detector arranged and configured to detect blood; an integrated inertial measurement unit (IMU) arranged and configured to detect movement of the limb, a patient's pulse, or a combination thereof; and a transmitter arranged and configured to transmit information or data relating to the detection of blood, movement of the limb, the patient's pulse, or a combination thereof, to the dialysis machine.

In one embodiment, upon detection of blood, the dialysis machine is arranged and configured to transmit an alert, cease operation of the dialysis treatment, or a combination thereof.

In one embodiment, upon determination of a change in pressure associated with the patient's pulse, the dialysis machine analyzes movement of the patient's limb via information or data from the IMU.

In one embodiment, upon determination of the change in pressure associated with the patient's pulse and movement of the patient's limb, the dialysis machine correlates the change in pressure with movement of the patient's limb and continues the dialysis treatment.

In one embodiment, upon determination of the change in pressure associated with the patient's pulse and lack of movement of the patient's limb, the dialysis machine transmits an alert, ceases operation of the dialysis treatment, or a combination thereof.

In one embodiment, the detector assembly further includes a housing enclosing a print-circuit-board, the IMU being positioned onto the print-circuit-board.

In one embodiment, the IMU is arranged and configured to measure the patient's pulse either by monitoring the patient's blood vessels or monitoring blood traveling through tubing of the dialysis system; or any combination thereof.

In one embodiment, the IMU is arranged and configured to monitor usage of the detector assembly.

In one embodiment, the dialysis machine is arranged and configured to monitor battery life of the detector based on information or data received from the IMU.

A wireless, battery-powered detector assembly is also disclosed. The detector assembly being arranged and configured to couple to a patient's limb adjacent to a blood access point during a dialysis treatment. In one embodiment, the detector assembly comprises a wetness detector arranged and configured to detect blood; an integrated inertial measurement unit (IMU) arranged and configured to detect movement of a patient's limb, a patient's pulse, or a combination thereof; and a transmitter arranged and configured to transmit information or data relating to the detection of blood, movement of the patient's limb, the patient's pulse, or a combination thereof, to a dialysis machine.

In one embodiment, the detector assembly includes a housing enclosing a print-circuit-board, the IMU being positioned onto the print-circuit-board.

In one embodiment, the IMU is arranged and configured to measure the patient's pulse either by monitoring the patient's blood vessels or monitoring blood traveling through tubing of a dialysis system; or any combination thereof.

In one embodiment, the IMU is arranged and configured to transmit information or data pertaining to usage of the detector assembly.

In one embodiment, the IMU is arranged and configured to transmit information or data pertaining to battery life.

A method for monitoring a patient during a dialysis treatment utilizing a dialysis machine is also disclosed. In one embodiment, the method comprises positioning a detector assembly adjacent to a blood access point on a patient's limb; monitoring, via the detector assembly, the patient's limb adjacent to the blood access point for wetness; monitoring, via the dialysis machine blood tubing pressure; monitoring, via the detector assembly, changes in blood tubing pressure; monitoring, via the detector assembly, movement of the patient's limb; and upon detection of blood, transmitting an alert, ceasing operation of the dialysis treatment, or a combination thereof.

In one embodiment, upon determination of changes in pressure, analyzing movement of the patient's limb.

In one embodiment, upon determination of changes in pressure and movement of the patient's limb, the dialysis machine correlates the changes in pressure with movement of the patient's limb and continues the dialysis treatment.

In one embodiment, upon determination of changes in pressure and lack of movement of the patient's limb, the dialysis machine transmits the alert, ceases operation of the dialysis treatment, or a combination thereof.

BRIEF DESCRIPTION OF THE DRAWINGS

By way of example, specific embodiments of the disclosed methods and devices will now be described, with reference to the accompanying drawings, in which.

DETAILED DESCRIPTION

The present embodiments will now be described more fully hereinafter with reference to the accompanying drawings, in which several exemplary embodiments are shown. The subject matter of the present disclosure, however, may be embodied in many different forms and types of devices and systems for dialysis and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of an improved detector assembly arranged and configured for use in a dialysis system is disclosed herein. In accordance with one or more features of the present disclosure, the detector assembly includes one or more sensors arranged and configured to measure, read, obtain, provide, etc. information or data during a dialysis treatment, which information or data can be transmitted to the dialysis machine and interpreted or used to, for example, provide greater insight into the system and/or to facilitate improved decision making. In one embodiment, the detector assembly includes, or is operatively coupled with, a sensor such as, for example, a wetness sensor, arranged and configured to monitor and/or detect wetness, blood, a leak, etc.

In addition, in accordance with one or more features of the present disclosure, the detector assembly includes an inertial measurement unit (IMU) arranged and configured to monitor and/or detect movement. Moreover, the IMU can be utilized to monitor and/or detect a patient's pulse (e.g., in one embodiment, the IMU can detect the patient's pulse by the rhythmic vibrations of the blood moving through the blood access point, that is, the IMU can monitor or measure the blood flow in the patient underneath the detector via detecting throbbing of the patient's blood vessels or by monitoring blood traveling through the tubing of the dialysis system (e.g., blood tubing pressure)). Thus arranged, in use, additional information or data relating to the patient's bodily movements and/or the detector assembly's movements can be obtained and utilized in the decision-making process. As such, in one embodiment, the detector assembly may be referred to as a wetness detector with an integrated IMU. For example, in use, the wetness detector with integrated IMU can be used to monitor a patient's movement and pulse, and to feed that information back to the dialysis machine and/or system to determine when and how a patient is moving during a pressure change in the patient's pulse.

While the present disclosure be described and illustrated in connection particular dialysis system and/or machine, it should be appreciated that the present disclosure is not so limited and should not be limited to any particular type of dialysis machine or system. Rather, it is envisioned that the present disclosure, and specifically the wetness detector with integrated IMU disclosed herein, may be used in connection with other types of dialysis machines or systems. For example, it is envisioned that the wetness detector with integrated IMU may also be used in connection with peritoneal dialysis (PD) systems wherein, as will be appreciated by one of ordinary skill in the art, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. In addition, and/or alternatively, it is envisioned that the IMU can be used in other non-hemodialysis implementations such as, for example, a nocturnal PD treatment to determine how often a patient gets up in the night to use the restroom or if a patient is sleep walking. Thus, the present disclosure should not be limited to any particular type of dialysis machine or system unless specifically claimed.

In accordance with one or more features of the present disclosure, the dialysis system may include an inertial measurement unit (IMU). In use, the IMU may be positioned onto a patient's body, preferably adjacent to the patient's blood access point AP for monitoring a patient's movement and a patient's pulse, which information or data can be feed back to, for example, the dialysis machine or a data monitoring system operatively associated with the dialysis machine, which can utilize the information or data to determine when and how a patient is moving during a change in pressure of the patient's pulse. As will be appreciated by one of ordinary skill in the art, in use, the IMU is arranged and configured to measure and report movement such as, for example, angular rate, acceleration, etc. In addition, and/or alternatively, the IMU can be used to monitor or measure a patient's pulse and/or pressure either by monitoring and/or measuring the rhythmic vibrations of the patient's blood moving through the blood access point or monitoring and/or measuring the patient's blood traveling through the tubing of the dialysis system (e.g., blood tubing pressure). In use, in one embodiment, a microprocessor associated with the dialysis machine and/or system, running a data filtering algorithm, can hone in on the pulse frequency picked up by the IMU and can be programmed to ignore large changes in a patient's pulse such as, for example, large changes in pulse caused by limb movements.

For example, in one embodiment, the IMU is arranged and configured to continually monitor or measure a patient's pulse and/or pressure. The information or data being transmitted back to the dialysis machine and/or system. In use, the dialysis machine and/or system is arranged and configured to continually monitor the patient's pulse and/or the pressure of the arterial and venous bloodlines for either an abrupt change in pressure or a slow departure from soft and hard pressure limits that could indicate clotting, kinks in the tubing, or a potential needle dislodgement. Thereafter, as will be described in greater detail herein, when an abrupt change in pressure or a slow departure from soft and hard pressure limits are detected, the dialysis machine and/or system, using additional information regarding patient movement collected by the IMU, can be used to determine if triggering an alert and/or stoppage of dialysis treatment is needed, or if the change in pressure can be ignored and the dialysis treatment continued.

Figure 4A:
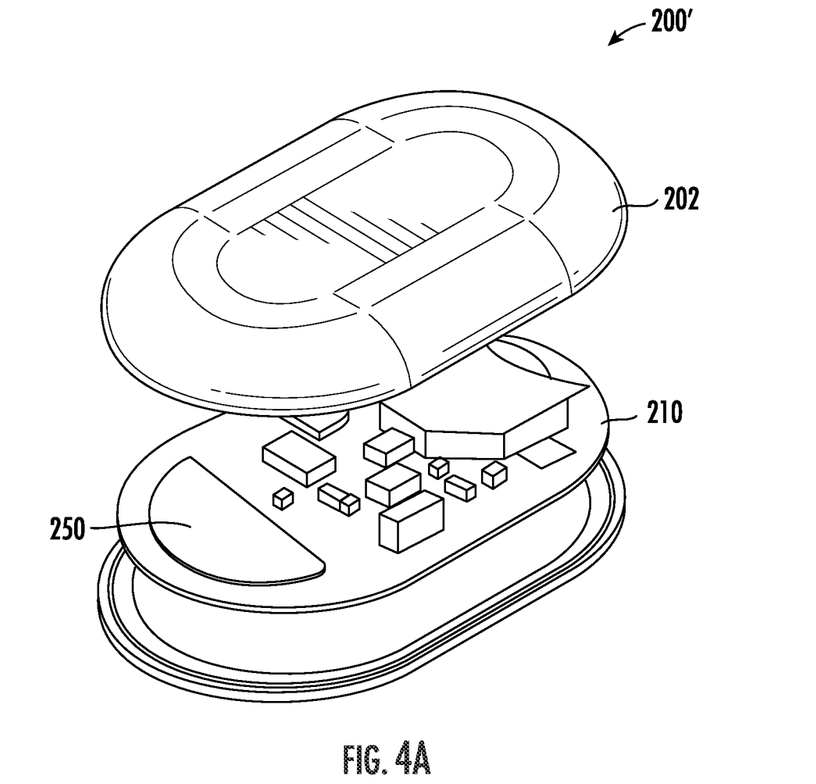
FIG. 4A illustrates an exploded view of an example embodiment of a detector assembly including a wetness detector with an integrated inertial measurement unit in accordance with one or more features of the present disclosure.
Figure 4B:
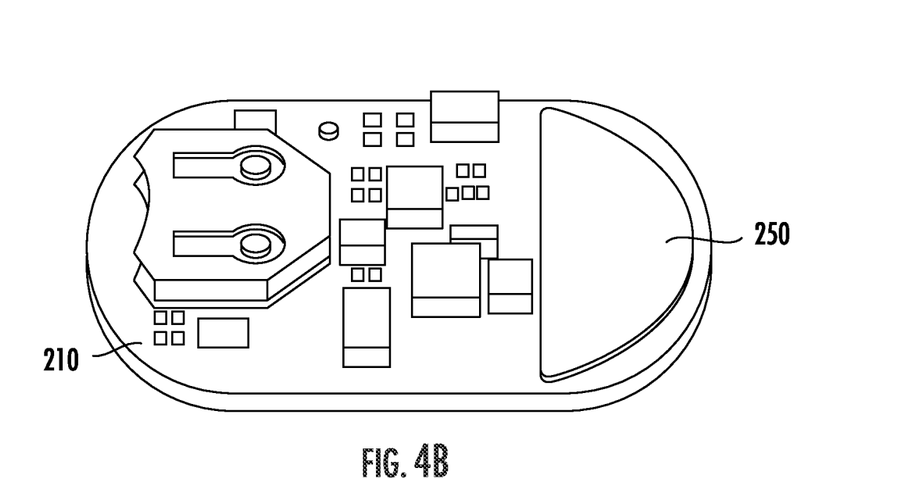
FIG. 4B illustrates a perspective view of a print-circuit-board of the detector assembly shown in FIG. 4A.

Referring to FIGS. 4A and 4B, in one embodiment, the IMU 250 may be incorporated directly into the wetness detector 200' such as, for example, integrated onto a print-circuit-board (PCB) 210 of the wetness detector 200' thereby providing a wetness detector with integrated IMU. That is, the wetness detector 200' may include a housing 202 enclosing a PCB 210. In one embodiment, the IMU 250 may be included onto the PCB 210, which also includes the wetness sensor.

In use, the IMU 250 may be any suitable IMU now know or hereafter developed. For example, in one embodiment, the IMU 250 may be one of the iNEMO inertial modules manufactured by STMicroelectronics. By integrating the IMU 250 into the wetness detector 200' both sensors can be incorporated into the same form factor, with the device including both sensors ideally positioned adjacent to the patient's blood access point AP. In addition, the device including both sensors can utilize the same wireless transmitter for sending and receiving information or data to the paired dialysis machine.

In one embodiment, the wetness detector 200' with integrated IMU 250 can be arranged and configured to determine or measure, inter alia, presence of wetness, blood, a leak, etc.; a patient's pulse; patient movement; or any combination thereof.

In accordance with one or more features of the present disclosure, by incorporating an IMU 250 into the dialysis system, and more preferably into the wetness detector 200' positioned adjacent to the patient's blood access point AP, the dialysis machine and/or system can determine whether a patient is moving at the same time as when a signal anomaly occurs such as, for example, a signal anomaly caused by a large pressure change in a patient's pulse that falls outside of a predetermined allowable range (e.g., outside soft and hard pressure limits), and if so, the signal anomaly can be determined to be caused by patient movement and thus ignored. In addition, the dialysis machine and/or system can correlate the magnitude of signal anomaly with the magnitude and type of patient movement. By measuring how and when the patient moves and comparing it against the signal anomaly, the anomalies can be explained and the hemodialysis machine can continue with the dialysis treatment without sounding a nuisance alarm.

That is, as previously described, in use, the dialysis machine and/or system may interpret pressure changes (e.g., changes in the patient's pulse) that fall outside of an allowable range as a potential needle dislodgement causing a signal anomaly to be transmitted causing an alert to the operator and/or stoppage of the dialysis treatment. Thus, currently, for example, if the patient raises or lowers his arm during a dialysis treatment, this movement (e.g., pressure change) may be interpreted by the dialysis machine and/or system to be a needle dislodgement causing the dialysis machine and/or system to transmit an alarm and/or cease dialysis treatment. However, in accordance with one or more features of the present disclosure, by incorporating an IMU 250 into the detector assembly 200', the dialysis machine and/or system can receive information or data pertaining to the patient's movements at the time it receives information or data relating to the patient's pulse and based on the collective information or data received, determine if a needle dislodgement has in fact occurred.

For example, in one scenario, if the patient moves during a dialysis treatment (e.g., if the IMU detects patient movement), the wetness detector 200' with integrated IMU 250 can transmit signals to the dialysis machine and/or system regarding the patient movement. The signal can include (i) whether or not the wetness sensor detects fluid, blood, a leak, etc., (ii) the patient's pulse, and (iii) motion detection from the IMU. As such, with information and data pertaining to wetness, pulse, and motion, the dialysis machine and/or system can make a more informed decision as to whether or not a needle dislodgement has occurred triggering an alert and/or stoppage of dialysis treatment. For example, if the wetness detector detects fluid, blood, a leak, etc., this information can automatically trigger the dialysis machine and/or system to transmit an alert and cease operation of the dialysis treatment. However, if the dialysis machine and/or system, based on information or data received from the detector assembly, determines a large pressure change and determines that the patient's limb was moving just prior to or at the same time as the large change in pressure, the dialysis machine can analyze this information as resulting from patient movement and not a needle dislodgement, thus no alert is transmitted and the dialysis treatment may continue. If, however, the dialysis machine and/or system, based on information or data received from the detector assembly, determines a large pressure change and determines that the patient's limb was not moving just prior to or at the same time as the large change in pressure, the dialysis machine can analyze this information as a potential needle dislodgement causing triggering of an alert and/or stoppage of dialysis treatment.

Thus arranged, the IMU can be used to provide another stream of information or data that can be used by the dialysis machine and/or system to interpret what is going on with the patient, which information or data can be used to better determine if a needle dislodgement has occurred thereby preventing, or at least reducing the number of nuisance alarms.

Additional benefits of incorporating an IMU 250 into the wetness detector 200' may be obtained. For example, positional information or data can be obtained using the wetness detector with integrated IMU. That is, the location of the wetness detector with integrated IMU can now be tracked by the dialysis machine and/or system to determine the location of the wetness detector 200'. For example, static readings, the thrill of the patient's pulse, sudden movement of the detector assembly, etc. all have unique motions or signals that can be used by the dialysis machine and/or system. For example, if the detector assembly has been placed on the floor and subsequent movement is detected, the dialysis machine and/or system can interpret this to indicate that the detector assembly has been kicked or relocated and confirm the action with the operator. Alternatively, if the detector assembly has been positioned adjacent to the patient's blood access site, the micro movements of the blood pulsing through the A/V graft or fistula can be compared to the pressure changes in the bloodline to improve safety by narrowing limits intelligently and automatically open them when the detector assembly senses the patient is moving his access limb. Moreover, if the dialysis machine and/or system previously detected the detector assembly on the patient's access limb and then notices a sudden change, the dialysis machine and/or system can be programmed to interpret this as if the detector assembly is falling and as a result, it can notify the operator that the access site is no longer being monitored by the detector assembly. These are just some examples of how the wetness detector with integrated IMU can collect additional information or data and how the dialysis machine and/or system can be programmed to interpret that information or data to make more intelligent decisions to enhance safety and awareness.

The IMU 250 can also be used to assist with monitoring usage of the detector assembly 200'. For example, currently, once a battery is inserted into a detector assembly, manufacturers have no idea how long the detector assembly may sit on a shelf or how frequently the detector assembly may be used, or even how long the detector assembly may be used past its recommended life. By incorporating an IMU into the wetness detector, additional information may be gained. For example, if a detector assembly is sitting on a shelf in a clinic, it has a very different motion profile from one used multiple times per week. By monitoring how often a detector assembly is used (e.g., moves), manufacturers can gain insights in the popularity of the detector assembly, whether or not patients are using it, and how many months the same detector assembly is being used before disposing of it due to a spent battery, with the detector assembly's unique ID piggybacking on the dialysis machine's status report. For example, each detector assembly may be embedded with a unique Id indicating date of manufacture. Upon coupling (e.g., pairing if wirelessly coupled) with a dialysis machine, the detector assembly can transmit information or data relating to the Id, and hence date of manufacture, allowing the dialysis machine and/or system to determine how long the detector assembly was sitting on a self and/or calculate battery depletion, and thus remaining battery life. Alternatively, the dialysis machine and/or system can track how long and/or often the detector assembly is being used by monitoring movement of the detector assembly.

In addition, and/or alternatively, the IMU can be used to infer other patient characteristics such as, for example, patient activity can be inferred based on how much movement occurs while the patient is sitting in a dialysis chair. For example, if the patient is nearly motionless, it is a good indicator that they are lethargic, not snacking, and/or not very engaged in their treatment. As a result, client follow-up can be triggered to see if the patient experience can be improved or if changes to the patient's treatment are needed.

In addition, and/or alternatively, it is envisioned that the wetness detector and integrated IMU may incorporate additional sensors to provide even more information or data. For example, the detector assembly may incorporate a temperature sensor, an ultrasonic or vibration sensor, a voltage regulator, or any combination thereof. In use, the temperature sensor can be used to detect fluctuation in access temperature that may be indicative of recirculation and, therefore, inadequate dialysis. This information can be fed back to the dialysis machine and/or system to provide better insights into patient treatment. An ultrasonic or vibration sensor can be used to detect anomalies in the patient's heartbeat to monitor for cardiac health and alert the dialysis machine and remotely monitoring clinic of a potential stroke or heart attack episode in the patient. A voltage regulator can be used to monitor shelf-life and battery life to inform operators via the dialysis machine and/or system.

In accordance with one or more features of the present disclosure, by incorporating an IMU sensor and, more preferably, by integrating an IMU sensor into an existing wetness detector, the wetness detector with integrated IMU can capitalize on a critical sensor location already in use to reduce nuisance alarms by providing additional streams of information or data to be used when signal anomalies (e.g., changes in a patient's pulse) are received.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The foregoing discussion has been presented for purposes of illustration and description and is not intended to limit the disclosure to the form or forms disclosed herein. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. In addition, while certain embodiments have been described and illustrated with certain features, it is envisioned that features of one embodiment may be used in combination with other embodiments. Moreover, the following claims are hereby incorporated into this Detailed Description by this reference, with each claim standing on its own as a separate embodiment of the present disclosure.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A dialysis system for providing a dialysis treatment to a patient, the dialysis system comprising:
    a dialysis machine including a dialysate flow path;
    an extracorporeal blood flow path including a connector coupled to a limb of the patient at a blood access point;
    a dialyzer arranged and configured to receive dialysate from the dialysate flow path and blood from the extracorporeal blood flow path; and
    a detector assembly coupled to the limb of the patient adjacent to the blood access point, the detector assembly including:
        a wetness detector arranged and configured to detect blood;
        an integrated inertial measurement unit (IMU) arranged and configured to detect a patient's pulse; and
        a transmitter arranged and configured to transmit information or data relating to the detection of blood, movement of the limb, the patient's pulse, or a combination thereof, to the dialysis machine;
    wherein the IMU is arranged and configured to measure the patient's pulse either by monitoring the patient's blood vessels or monitoring blood traveling through tubing of the dialysis system; or any combination thereof.

2. The dialysis system of claim 1, wherein upon detection of blood, the dialysis machine is arranged and configured to transmit an alert, cease operation of the dialysis treatment, or a combination thereof.

3. The dialysis system of claim 2, wherein upon determination of a change in pressure associated with the patient's pulse, the dialysis machine analyzes movement of the patient's limb via information or data from the IMU.

4. The dialysis system of claim 3, wherein upon determination of the change in pressure associated with the patient's pulse and movement of the patient's limb, the dialysis machine correlates the change in pressure with movement of the patient's limb and continues the dialysis treatment.

5. The dialysis system of claim 3, wherein upon determination of the change in pressure associated with the patient's pulse and lack of movement of the patient's limb, the dialysis machine transmits an alert, ceases operation of the dialysis treatment, or a combination thereof.

6. The dialysis system of claim 1, wherein the detector assembly further includes a housing enclosing a print-circuit-board, the IMU being positioned onto the print-circuit-board.

7. The dialysis system of claim 1, wherein the IMU is arranged and configured to monitor usage of the detector assembly.

8. The dialysis system of claim 7, wherein the dialysis machine is arranged and configured to monitor battery life of the detector based on information or data received from the IMU.

9. A wireless, battery-powered detector assembly arranged and configured to couple to a patient's limb adjacent to a blood access point during a dialysis treatment, the detector assembly comprising:
    a wetness detector arranged and configured to detect blood;
    an integrated inertial measurement unit (IMU) arranged and configured to detect a patient's pulse; and
    a transmitter arranged and configured to transmit information or data relating to the detection of blood, movement of the patient's limb, the patient's pulse, or a combination thereof, to a dialysis machines;
    wherein the IMU is arranged and configured to measure the patient's pulse either by monitoring the patient's blood vessels or monitoring blood traveling through tubing of a dialysis system; or any combination thereof.

10. The detector assembly of claim 9, wherein the detector assembly includes a housing enclosing a print-circuit-board, the IMU being positioned onto the print-circuit-board.

11. The detector assembly of claim 9, wherein the IMU is arranged and configured to transmit information or data pertaining to usage of the detector assembly.

12. The detector assembly of claim 11, wherein the IMU is arranged and configured to transmit information or data pertaining to battery life.

* * * * *